United States Patent
Wolf et al.

(10) Patent No.: US 7,947,506 B2
(45) Date of Patent: May 24, 2011

(54) PROTEIN DETECTION AND QUANTITATION USING HYDROXYQUINOLONE DYES

(75) Inventors: Brian David Wolf, Machesney Park, IL (US); Surbhi Desai, Rockford, IL (US); Peter T. Czerney, Weimar (DE); Frank G. Lehmann, Jena (DE); Bernd G. Schweder, Jena (DE); Matthias S. Wenzel, Jena (DE)

(73) Assignee: Pierce Biotechnology, Inc., Rockford, IL (US)

( * ) Notice: Subject to any disclaimer, the term of this patent is extended or adjusted under 35 U.S.C. 154(b) by 421 days.

(21) Appl. No.: 11/421,883

(22) Filed: Jun. 2, 2006

(65) Prior Publication Data

US 2007/0281360 A1 Dec. 6, 2007

(51) Int. Cl.
- *G01N 33/00* (2006.01)
- *G01N 33/58* (2006.01)
- *C12Q 1/68* (2006.01)
- *C09B 23/00* (2006.01)
- *C09B 57/02* (2006.01)

(52) U.S. Cl. ........... 436/86; 546/66; 546/89; 546/99; 546/148; 546/176; 435/6; 435/7.1; 548/121; 548/148; 548/159; 548/217

(58) Field of Classification Search .............. 436/86
See application file for complete search history.

(56) References Cited

U.S. PATENT DOCUMENTS

| 6,316,267 B1 * | 11/2001 | Bhalgat et al. ........ 436/86 |
| 2003/0165942 A1 | 9/2003 | Czerney et al. |
| 2004/0260093 A1 | 12/2004 | Czerney et al. |
| 2006/0166368 A1 | 7/2006 | Berklemen |

FOREIGN PATENT DOCUMENTS

WO   WO 2006/079334   8/2006

OTHER PUBLICATIONS

International Search Report, dated Sep. 26, 2007, WO 2006/079334.

* cited by examiner

*Primary Examiner* — Krishnan S Menon
*Assistant Examiner* — Dirk Bass
(74) *Attorney, Agent, or Firm* — Thompson Hine LLP

(57) ABSTRACT

A hydroxyquinolone compound formulated as a fluorescent dye for protein detection, assay, quantitation, etc. The hydroxyquinolone compound may be modified, for example, by adding or removing sulfate groups, changing hydrocarbon chain lengths, etc. to result in more desirable properties such as enhanced binding to basic proteins, enhanced solubility, etc. The dye has enhanced sensitivity over commercially available protein stains, and may be used to stain proteins in solution, proteins separated on gels, proteins transferred to solid supports, etc. Methods of using the dyes are also disclosed.

8 Claims, 23 Drawing Sheets

| | Compound #4 | Compound #4 (Rapid) | Flamingo | SYPRO Ruby Overnight | SYPRO Microwave | Deep Purple |
|---|---|---|---|---|---|---|
| Fix | 60 | 10 | 120 | 60 | 30 | 60 |
| Wash | 5 | 1 | 0 | 0 | 0 | 30 |
| Stain | 60 | 15 | 180 | 720 | 30 | 60 |
| Destain | 5 | 0 | 10 | 30 | 30 | 30 |
| Wash | 30 | 3 | 20 | 10 | 10 | 10 |
| Total Minutes | 160 | 29 | 330 | 820 | 100 | 190 |

A          B

A  B

A  B

PROTEIN DETECTION AND QUANTITATION USING HYDROXYQUINOLONE DYES

FIELD OF THE INVENTION

Uses of hydroxyquinolone compounds as fluorescent dyes for protein detection and quantitation.

BACKGROUND

Proteins separated by electrophoresis in a gel or following transfer to a membrane have traditionally been detected using visible organic dyes. The detection limit using chromogenic dyes such as Coomassie G250 or Coomassie R250 is generally in the range of 1 ng to 10 ng. Fluorescent methods of protein detection offer good sensitivities and multiplexing capabilities. For example, they allow detection of a post-translationally modified protein such as a glycoprotein with a specific stain in combination with a total protein stain. Such fluorescent dyes and their methods of use in protein detection and quantitation are desirable.

DETAILED DESCRIPTION

Figure 1:
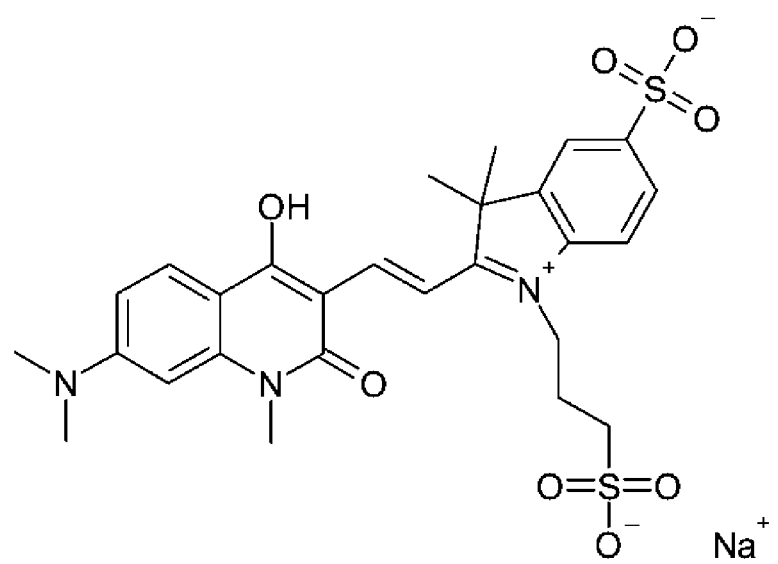
FIG. 1 shows the structure of one hydroxyquinolone compound designated #1 (V08-05106).
Figure 2:
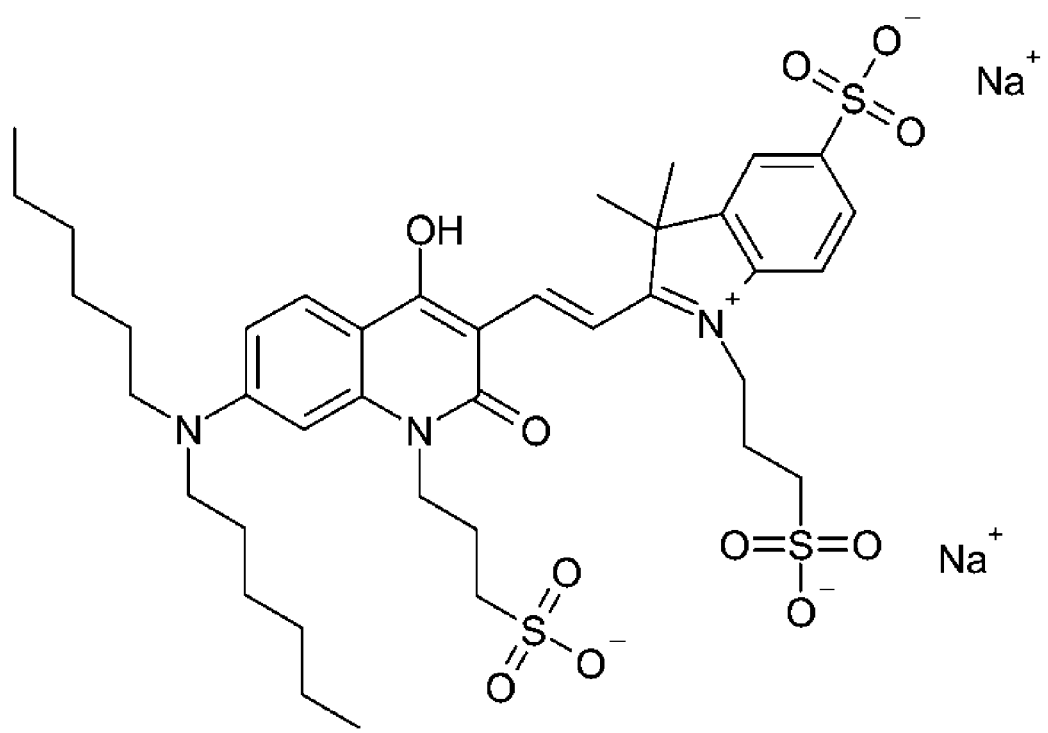
FIG. 2 shows the structure of another hydroxyquinolone compound designated #2 (V07-05155).
Figure 3:
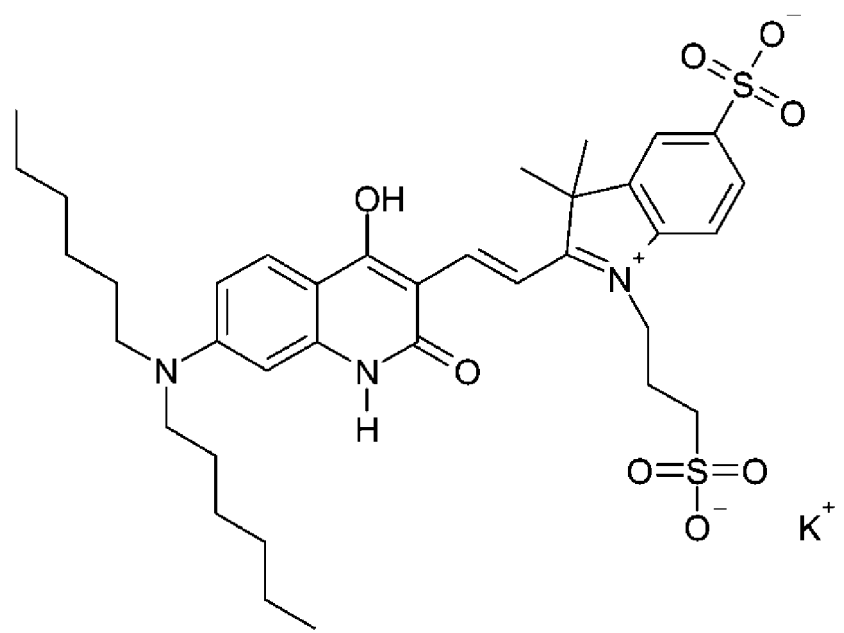
FIG. 3 shows the structure of another hydroxyquinolone compound designated #3 (V07-05158).
Figure 4:
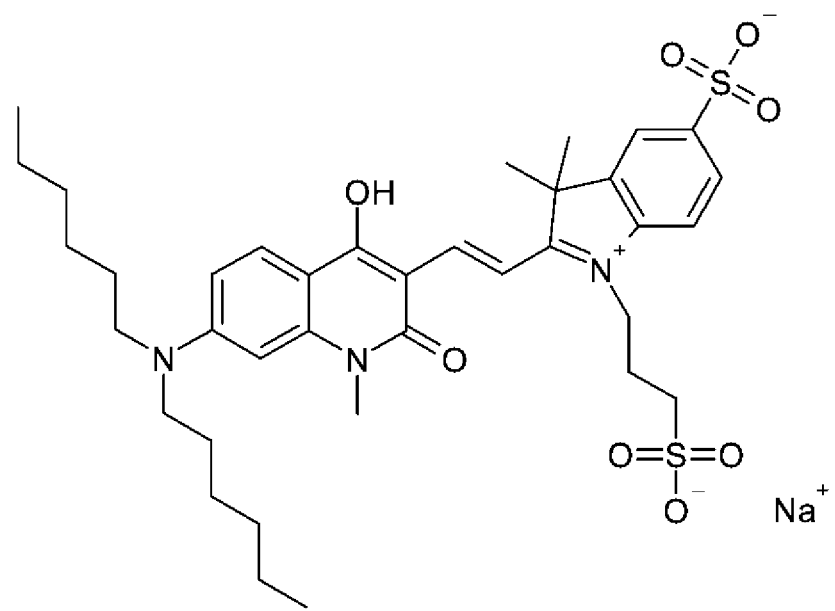
FIG. 4 shows the structure of another hydroxyquinolone compound designated #4 (V07-05165).
Figure 5:
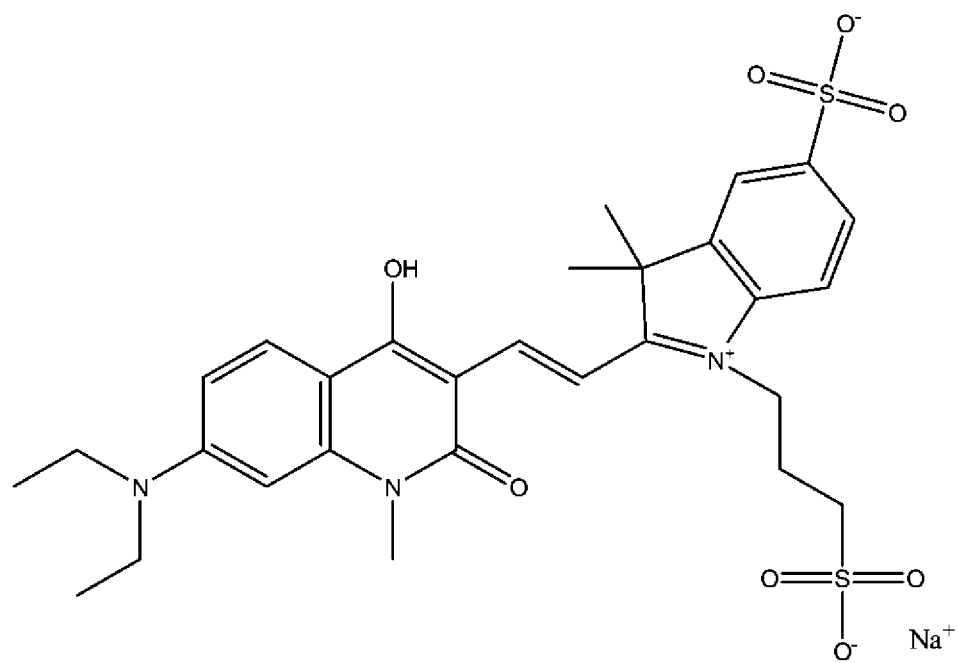
FIG. 5 shows the structure of another hydroxyquinolone compound designated #5 (V10-01018).

This application contains at least one drawing executed in color. A Petition under 37 C.F.R. §1.84 requesting acceptance of the color drawings is filed separately on even date herewith. Copies of this patent or patent application publication with color drawing(s) will be provided by the Office upon request and payment of the necessary fee.

A method is disclosed using a family of substituted hydroxyquinolone compounds, designated as compounds #1, #2, #3, #4, and #5 and shown in FIGS. 1, 2, 3, 4, and 5 respectively, and modifications of these compounds as subsequently described, formulated and used as fluorescent dyes (also referred to as stains) for protein detection, quantitation, stain, assay, etc. These hydroxyquinolone compounds formulated as dyes, also referred to as hydroxyquinolone dyes, detect proteins and/or amino acids with a sensitivity of less than 1 ng. The fluorescence of hydroxyquinolone dyes increases when the dye is bound to protein. Such dyes result in increased sensitivity, ease of use, decreased background, and more accurate results over other protein detection and assay reagents, such as heavy metal-based complexes.

The disclosed method encompasses any qualitative and/or quantitative determination of the presence, characterization, function, etc. of one or more peptides and/or proteins. One or more hydroxyquinolone dyes bind to proteins in solution or proteins that have been separated from a mixture. Proteins may be separated by polyacrylamide gel electrophoresis followed by a wash/fix procedure and detected and/or assayed in the gel. Alternatively, separated proteins may be transferred to a membrane and detected and/or separated in the membrane. Additionally, these dyes may be used to quantitate proteins in solution.

A solution of the hydroxyquinolone dye(s) is applied to separated proteins or added to a protein solution and incubated for a time sufficient to stain the proteins. In one embodiment, incubation may be for about one hour. After incubation, the hydroxyquinolone dye(s) bound to proteins are detected directly or indirectly, and by any method (e.g., visually, by qualitative and/or quantitative scanning using a fluorescent imaging system, etc.). In embodiments where proteins are separated, the gel or membrane is washed with water or a dilute alcohol/acid mixture before dye incubation.

Modifications to compounds #1, #2, #3, #4, and #5 are encompassed by the method, as appreciated by one skilled in the art. Modifications include substitutions, derivatives, additions, deletions, etc. of one or more compound constituent and/or salt, and may be in the hydroxyquinolone structure, the indole ring, the benzene ring, the hydrocarbon chains, the sulfonate groups, etc. In one embodiment, the disclosed hydroxyquinolone compounds are modified for detection in the visible and/or the infrared (IR) region of the electromagnetic spectrum. For example, increasing the length of the alkene linker between ring structures results in a compound that, when formulated as a dye, is detectable in the IR region. In another embodiment, the hydroxyquinolone compounds may be non-, mono-, di-, or tri-sulfonated. In another embodiment, nitrogen in the hydroxyquinolone ring may be substituted with H, methyl, ethyl, or other hydrocarbon chains, or a sulfonate group. In another embodiment, nitrogen in the indole ring and/or carbon in the benzene ring may be substituted with alkylsulfonate or sulfonate groups, resulting in a dye with enhanced polarity. In another embodiment, adding long hydrocarbon chains on the nitrogen attached to the benzene ring of the hydroxyquinolone enhances its polarity and hence increases sensitivity of the dye. In another embodiment, adding a N,N-di-hexylamino function in the 7-position to the hydroxyquinolone ring increases binding of the dye and results in enhanced staining of hydrophobic amino acids.

Selected physical characteristics of the hydroxyquinolone dyes shown in FIGS. 1-5 are presented in Table 1.

(compounds #2, #3, and #4), the dyes also bound weakly to hydrophobic amino acid side chains (FIG. 6A). Dyes containing hydrophobic alkyl chains (7-N,N-dihexylamino substituted compounds #2, #3, and #4) had less protein-to-protein variable staining because the dyes bound to a broader range of amino acid side groups. Adding hydrophobic alkyl groups and alkylsulfonates (as in compound #2) to the base hydroxyquinolone structure (compound #1) enhanced protein binding and decreased background signal (dye binding to a polyacrylamide gel or nitrocellulose membrane). Compounds #3 and #4 have a hydrophobic 7-N,N-dihexylamino function in the 7-position that resulted in an increased binding to hydrophobic amino acids (red boxes in FIG. 6A) and the ability to detect spots containing 0.5 ng lysozyme. However, the background was higher with compounds #3 and #4 (FIG. 6B) compared to compounds #1 and #2.

The addition of N-alkylsulfonate groups, for example in compound #2, reduced background staining. Compound #1 lacks a hydrophobic 7-N,N-dihexylamino function. Without being bound by a specific theory, the addition of sulfonates may cause the compound to be more hydrophilic overall, resulting in lower background and reduced detection sensitivity (about 50 ng). Compound #2 offers a balance between the hydrophobic alkyl chains and sulfonates by adding a third sulfonate through a sulfo-alkyl group substituted on the hydroxyquinolone ring nitrogen. Compound #2 showed decreased background (FIG. 6B) compared to compounds #3 and #4, and increased detection over compound #1 (FIGS. 6A, 6C). For detection of proteins on a membrane, compound

TABLE 1

|  | MW | Molar Absorbance E (in MeOH) | Absorption Max. $\lambda_{abs}$ (in MeOH) | Emission Max. $\lambda_{em}$ (in MeOH) |
| --- | --- | --- | --- | --- |
| Compound #1 (V08-05106) | 611.67 g/mol | 110,000 mol$^{-1}$ cm$^{-1}$ | 508 nm | 560 nm |
| Compound #2 (V07-05155) | 882.04 g/mol | 65,000 mol$^{-1}$ cm$^{-1}$ | 516 nm | 598 nm |
| Compound #3 (V07-05158) | 754.03 g/mol | 107,000 mol$^{-1}$ cm$^{-1}$ | 513 nm | 580 nm |
| Compound #4 (V07-05165) | 751.94 g/mol | 105,000 mol$^{-1}$ cm$^{-1}$ | 513 nm | 580 nm |
| Compound #5 (V10-01018) | 639.73 g/mol | 80,000 mol$^{-1}$ cm$^{-1}$ | 513 nm | 580 nm |

Figure 6:
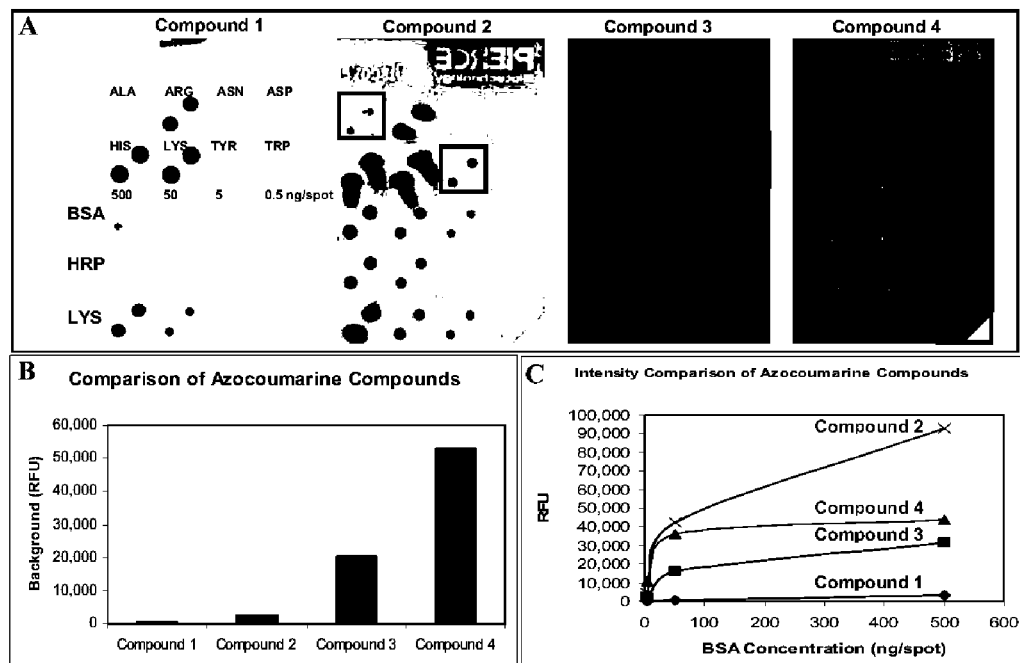
FIG. 6 shows use of hydroxyquinolone compounds as dyes to stain amino acids and proteins spotted on membranes.

FIG. 6 shows staining of amino acids and proteins on membranes using hydroxyquinolone dyes to which hydrophobic alkyl and alkylsulfonate groups were added. FIG. 6A shows staining of polymers of single amino acids (e.g., poly-alanine, poly-histidine, poly-lysine, etc.) and proteins. Selected polymers of single amino acids (200 ng/spot) and proteins (500 ng/spot, 50 ng/spot, 5 ng/spot, and 0.5 ng/spot) were spotted onto nitrocellulose membranes (for amino acids: ALA alanine; ARG arginine; ASN asparagine; ASP aspartic acid; HIS histidine; LYS lysine; TYR tyrosine; TRP tryptophan, for proteins BSA bovine serum albumin; HRP horseradish peroxidase; Lys lysozyme). The membranes were stained with the hydroxyquinolone dyes dissolved in water at 100 ng/ml. FIG. 6B is a graph showing background staining of dyes containing compounds #1, #2, #3, and #4, respectively. FIG. 6C is a graph showing relative intensities for these dyes.

Each of the hydroxyquinolone dyes (#1, #2, #3, #4, #5) stained basic amino acids (lysine, histidine, and arginine). With the addition of the 7-N,N-di-hexylamino function to the hydroxyquinolone ring, or other hydrophobic alkyl chains

2 exhibited the lowest background with the highest fluorescent intensity among all compounds evaluated (FIG. 6C).

Figure 7:
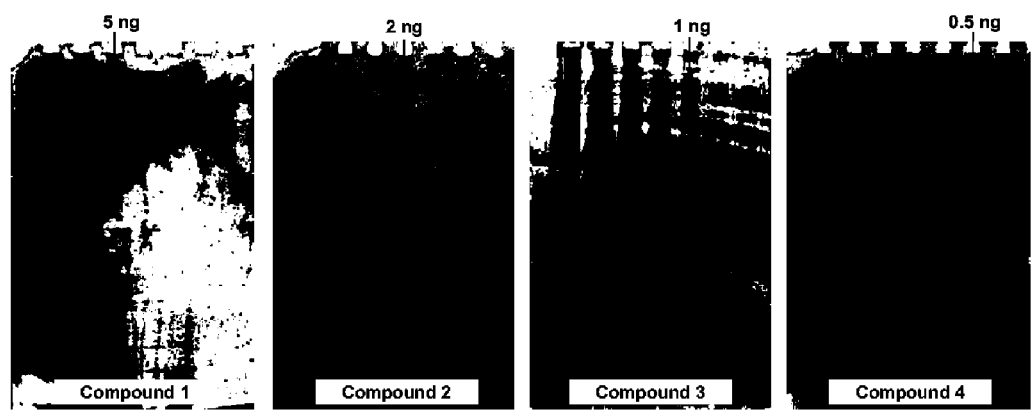
FIG. 7 shows use of hydroxyquinolone compounds as dyes to stain proteins that have been separated on gels.

Detection of proteins on a gel following electrophoresis was evaluated. A protein standard containing myosin, phosphorylase B, bovine serum albumin, horseradish peroxidase, carbonic anhydrase, myokinase, soybean trypsin inhibitor, and lysozyme was serially diluted. The proteins in the standard were separated by electrophoresis in 4-20% Precise Tris-HEPES (Pierce) gels and stained with hydroxyquinolone compounds #1, #2, #3, and #4 diluted in water at 100 ng/ml (FIG. 7). Compound #2, among the compounds evaluated, exhibited the highest detection of proteins on membranes. Compound #2 had a two fold reduced level of detection, about 2 ng, compared to compound #4, which was the most sensitive (0.5 ng) among the compounds evaluated on gels. Compound #4 exhibited a slight elevation in background signal but this did not interfere with detecting and visualizing protein bands.

Figure 20:
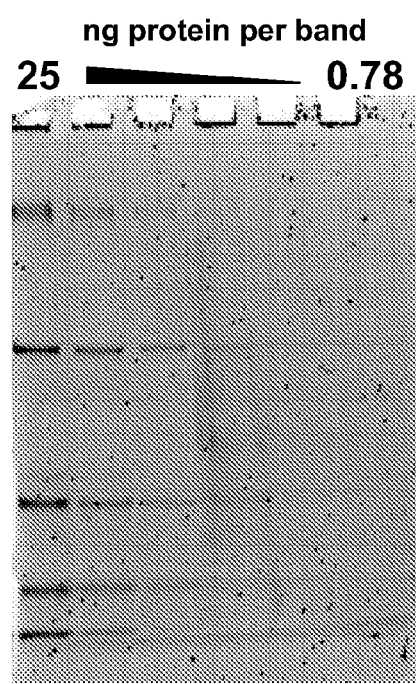
FIG. 20 shows the sensitivity of one hydroxyquinolone dye to detect proteins separated by electrophoresis.
Figure 21:
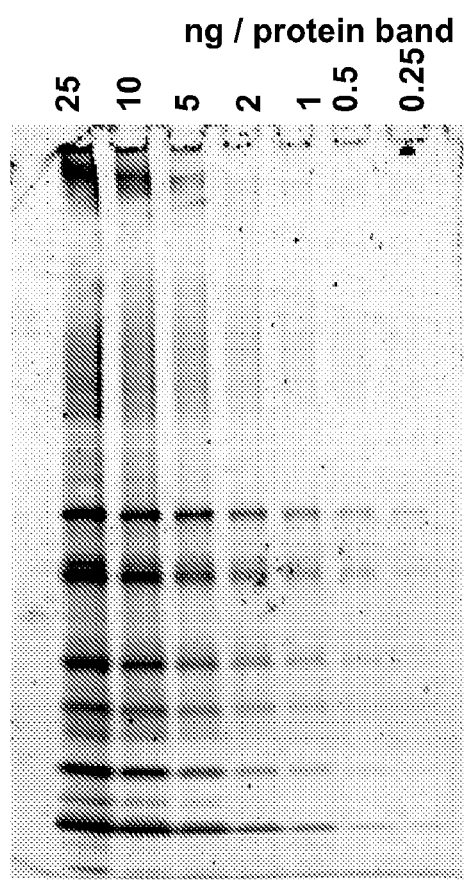
FIG. 21 shows one hydroxyquinolone dye staining proteins separated by electrophoresis on two different gels (FIG. 21A, 21B).
Figure 21:
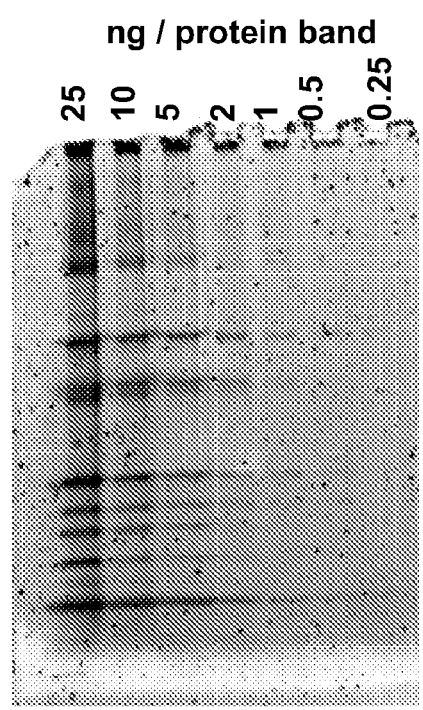
Figure 22:
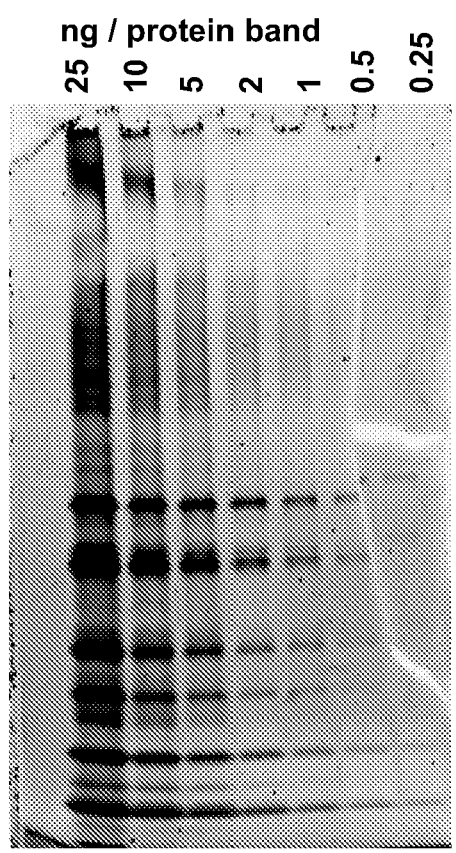
FIG. 22 shows another hydroxyquinolone dye staining proteins separated by electrophoresis on two different gels (FIG. 22A, FIG. 22B).
Figure 22:
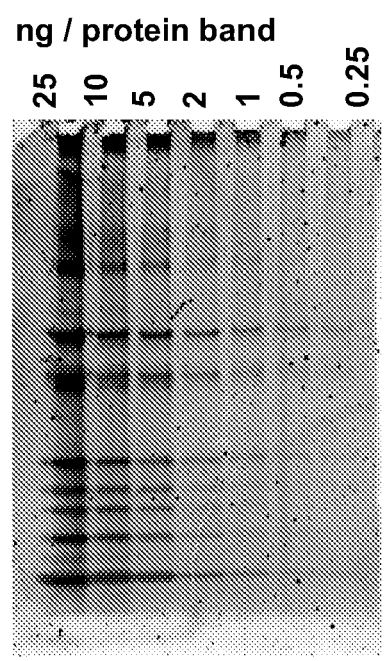
Figure 23:
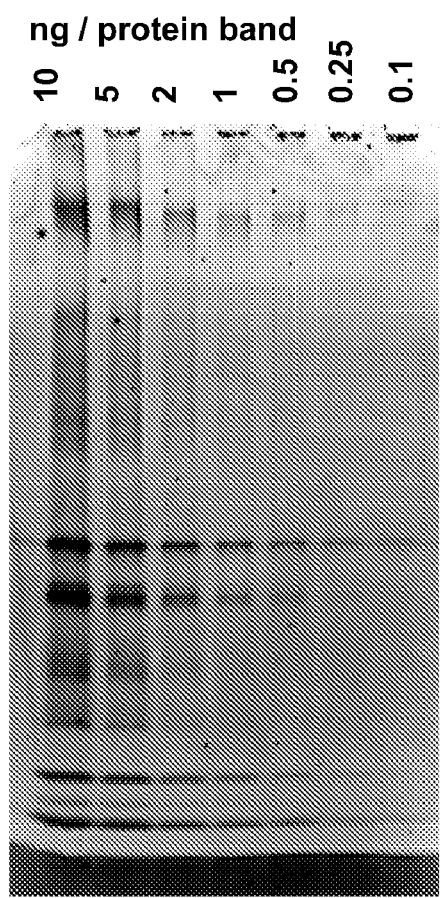
FIG. 23 shows one hydroxyquinolone dye staining proteins separated by electrophoresis under different conditions.
Figure 23:
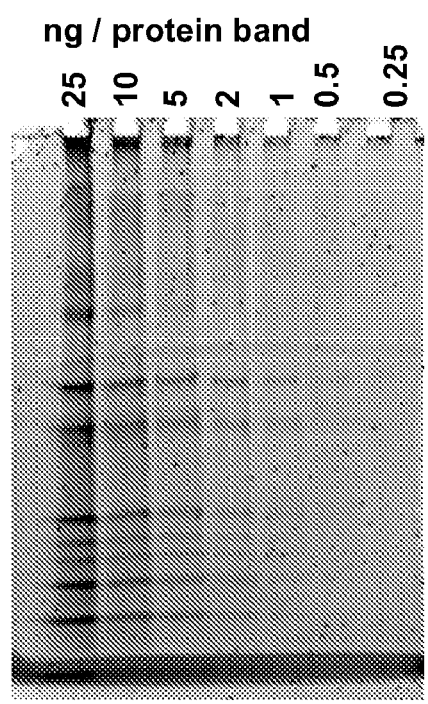

Compound #1 was able to detect proteins at a sensitivity of 3.9 ng while exhibiting relatively low background (FIG. 20). Compound #2 at a concentration of 100 ng/ml in 50 mM sodium propionate, pH 4, was able to detect proteins at a sensitivity of at least 0.25 ng when proteins were separated by electrophoresis on a 4-20% Tris-Glycine gel (Invitrogen), followed by a two hour destain in water (FIG. 21A). Using the same concentration, compound #2 was able to detect proteins at a sensitivity of at least 0.5 ng when proteins were separated by electrophoresis on a 4-20% Precise Tris-HEPES gel (Pierce) (FIG. 21B). Compound #3, at a concentration of 100 ng/ml in 50 mM sodium propionate, pH 4, was able to detect proteins at a sensitivity of at least 0.25 ng when proteins were separated by electrophoresis on a 4-20% Tris-glycine gel (Invitrogen), followed by a two hour destain in water (FIG. 22A). Using the same concentration, compound #3 was able to detect proteins at a sensitivity of at least 0.25 ng when proteins were separated by electrophoresis on a 4-20% Precise Tris-HEPES gel (Pierce) (FIG. 22B). Compound #4, at a concentration of 100 ng/ml in 50 mM 3-[cyclohexylamino]-1-propanesulfonic acid (CAPS), pH 10, was able to detect proteins at a sensitivity of at least 0.1 ng when proteins were separated by electrophoresis on a 4-20% Tris-glycine gel (Novex), followed by a thirty minute destain in water (FIG. 23A). Using the same concentration, compound #4 was able to detect proteins at a sensitivity of at least 0.25 ng when proteins were separated by electrophoresis on a 4-20% Precise Tris-HEPES gel, followed by a thirty minute destain in water (FIG. 23B).

Figure 8:
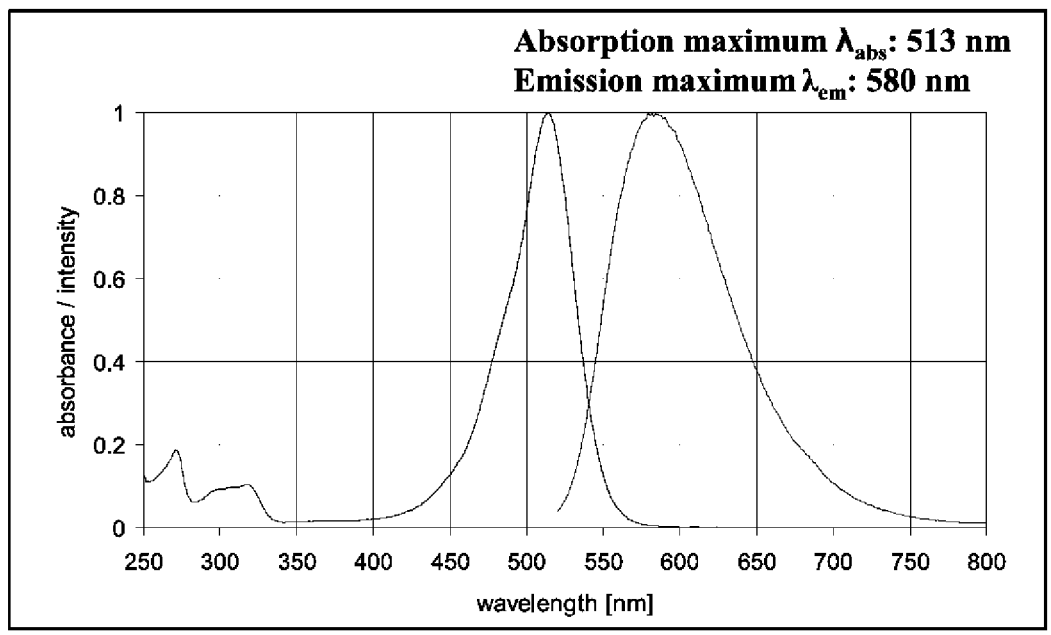
FIG. 8 shows the absorption and emission spectra of one hydroxyquinolone compound.

Compound #4, formulated as a hydroxyquinolone dye, embodiments of which were previously described, detected proteins at a sensitivity of about 0.25 ng/protein band or less, had a low background signal, and provided linear quantitative protein bands over three orders of magnitude on a logarithmic scale. Compound #4, when dissolved in methanol, has an absorption maximum s at 513 nm and an emission maximum at 580 nm (orange-red spectrum) (FIG. 8 and Table 1), making it compatible with 532 nm laser based scanners and other instruments having filter sets for the Cy3 wavelengths. The small absorbance peak in the UV (from 280 nm to 320 nm) region allowed the compound #4 dye to be visualized with UV lightboxes and transilluminators.

The working formulation of the fluorescent protein stain reagent may contain one or a combination of more than one of the hydroxyquinolone compounds disclosed in FIGS. 1-5 and/or modified as described, at concentrations ranging from about 25 nmol/L to about 200 nmol/L. In one embodiment, proteins separated by electrophoresis in a polyacrylamide matrix were stained with the hydroxyquinolone compound(s) at a concentration ranging from about 100 nmol/L to about 180 nmol/L. In another embodiment, proteins were stained with any of the compounds alone in a dye. In another embodiment, proteins were stained with a mixture of compounds in the dye, for example, compounds #2 and #4, compounds #4 and #3, compounds #4 and #5, compound #5 and #3, compounds #1, #4, and #2, compounds #2, #3, and #4, compounds #1, #2, #3, #4, and #5, etc.

The previously described hydroxyquinolone compounds, including modified hydroxyquinolone compounds, were formulated with excipients as protein dyes. For example, the compounds were compatible with a broad range of buffers over the pH range of about pH 3 to about pH 11. The following buffers can be used to enhance detection sensitivity (level of protein detection) and include, but are not limited to, short chain organic acids ($R-CO_2$) where R=H, $-CH_3$, $-CH_2-CH_3$, $-CH_2-CH_2-CH_3$, $-CH_2-CH_2-CH_2-CH_3$, etc, inorganic buffers such as phosphate and borate salts, and/or organic buffers such as TRIS (tris[hydroxymethyl]aminomethane hydrochloride), CAPS (3-[cyclohexylamino]-1-propanesulfonic acid), CHES (2-[cyclohexylamino)ethanesulfonic acid), MES (2-[N-morpholino]ethanesulfonic acid), HEPES (N-[2-hydroxyethyl]piperazine-N'-[2-ethanesulfonic acid]), and MOPS (3-[N-morpholino]propanesulfonic acid). The buffer concentration ranged from about 10 mM to about 1 M. In one embodiment, the pH ranged from about pH 3 to about pH 5. In another embodiment, the pH ranged from about pH 8 to about pH 10. In one embodiment, the buffer pH was adjusted using either sodium or potassium hydroxide.

Other components may be included as excipients. For example, additives that assist in solubilizing and stabilizing the hydroxyquinolone compound(s) in solution may be included. Examples of such additives that assist in solubilization, stabilization, and photostability include, but are not limited to, an alcohol ($R-OH$) at about 0.1% v/v to about 10% v/v such as methanol, ethanol or isopropanol; and/or a diol at about 1% v/v to about 10% v/v such as 1,2-propanediol, propane-1,3-diol, butane-1,2-diol, butane-1,3-diol, butane-1,4-diol, butane-2,3-diol, pentane-1,2-diol, pentane-1,3-diol, pentane-1,4-diol, pentane-1,5-diol, pentane-2,3-diol, pentane-2,4-diol, hexane-2,3-diol, and/or hexane-2,5-diol.

In one embodiment, the dye formulation may also contain benzaldehyde. For example, benzaldehyde at a concentration of at least 50 mM increased the absorbance and fluorescent intensity, dye stability, dye photostability, and detection sensitivity of hydroxyquinolone dyes. Fluorescence was preserved through extended washes.

The formulation may also contain polyethylene glycol (PEG) and/or polyvinyl alcohol (PVA) at about 0.1% v/v to about 5% v/v. Embodiments containing hydroxyquinolone compound(s) and PEG and/or PVA have reduced background, and thus provide enhanced sensitivity by increasing the signal to noise ratio.

The embodiments previously described were for a working 1× dye formulation used for staining proteins in a polyacrylamide gel or a solid support, such as nitrocellulose or PVDF, following transfer. The dye formulation may also be made and stored as a 10× solution. The 10× solution can be stored at about 4° C. to about 25° C. for an extended period, e.g., at least one year. In one embodiment, the 10× solution includes 550 mM sodium acetate, pH 4, 3% w/v polyethylene glycol, 50% v/v 1,2-propanediol, 4.9% v/v ethyl alcohol, 500 mM benzaldehyde, and 1.65 µM hydroxyquinolone compound (e.g., compound #1, #2, #3, #4, and/or #5, and including modifications of one or more compound(s) as previously described). Before staining proteins, the user dilutes the 10× solution 1 to 10 in water to prepare a 1× working solution that is then used to stain proteins in solution, on gels, membranes, etc.

The above described dyes can be used to stain proteins separated by electrophoresis in a gel in about 5 minutes to about 160 minutes. Following electrophoresis, the gels were washed in an alcohol ($R-OH$) at about 30% v/v to about 50% v/v, and acid ($R-CO_2$) at about 5% v/v to about 15% v/v, fixative solution. Examples of alcohols in the fixative solution include methanol, ethanol, and isopropanol and examples of acids in the fixative solution include formic acid, acetic acid, and proprionic acid. In one embodiment, the fixative solution is about 40% v/v ethanol and about 10% v/v acetic acid. The fixation step can be from about five minutes to overnight. In one embodiment, fixation involves two consecutive thirty minute washes in the fixative solution. Following fixation, the gel was washed in water for about five minutes to about fifteen minutes to remove any excess alcohol and/or acid. The 10× stain formulation (for example: 550 mM sodium acetate, pH 4, 3% w/v PEG, 4.9% v/v ethanol, 500 mM benzaldehyde, 50% v/v 1,2-propanediol, and 1.65 µM hydroxyquinolone compound(s) was diluted to a 1× working solution by combining one volume of the 10× staining reagent with nine volumes of water. A sufficient volume of the 1× working stain solution was used to completely cover the gel. Typically, 20 ml to 35 ml of fluorescent protein stain reagent solution is sufficient for an 8 cm×10 cm gel. The gel can be stained for a minimum of about five minutes, and may be stained as long as overnight. Longer incubation times in the stain provide greater fluorescent intensity and increase the level of protein detection. In one embodiment, the gel is incubated with the fluorescent protein stain reagent for about one hour to about two hours. Following staining, the gel is washed with acetic acid at about 5% v/v. The gel is then washed, or destained, in water for a minimum of about three minutes. Extended washing can be used but after about twelve hours, there was a decrease in the level of detection. In one embodiment, the destain procedure consisted of two consecutive fifteen minute washes in water. In another embodiment, the destain wash solution also included Tween-20 at a concentration of less than about 1% v/v. In another embodiment, the gel was destained with sodium carbonate solution at about 100 mM to 200 mM concentration and at about pH 9 to about pH 11.

The hydroxyquinolone dyes can also be used to quantitate proteins in solution. Formulations containing various concentrations of the hydroxyquinolones compounds (e.g., #1, #2, #3, #4, and/or #5, including modifications as previously described) may be added to protein solutions. In one embodiment, one volume of the protein solution is combined with 10 volumes of the dye formulation. In another embodiment, one volume of the protein solution is combined with one volume of the dye formulation. The resulting protein sample and dye formulation may be read instantly or after an incubation period. In one embodiment, the protein sample and dye formulation is incubated for about thirty minutes. The assay may be performed in multiple formats, including multiwell microtiterplates, tubes, etc., and read in appropriate fluorometers.

The method will be further appreciated with reference to the following examples.

Example 1

Figure 9:
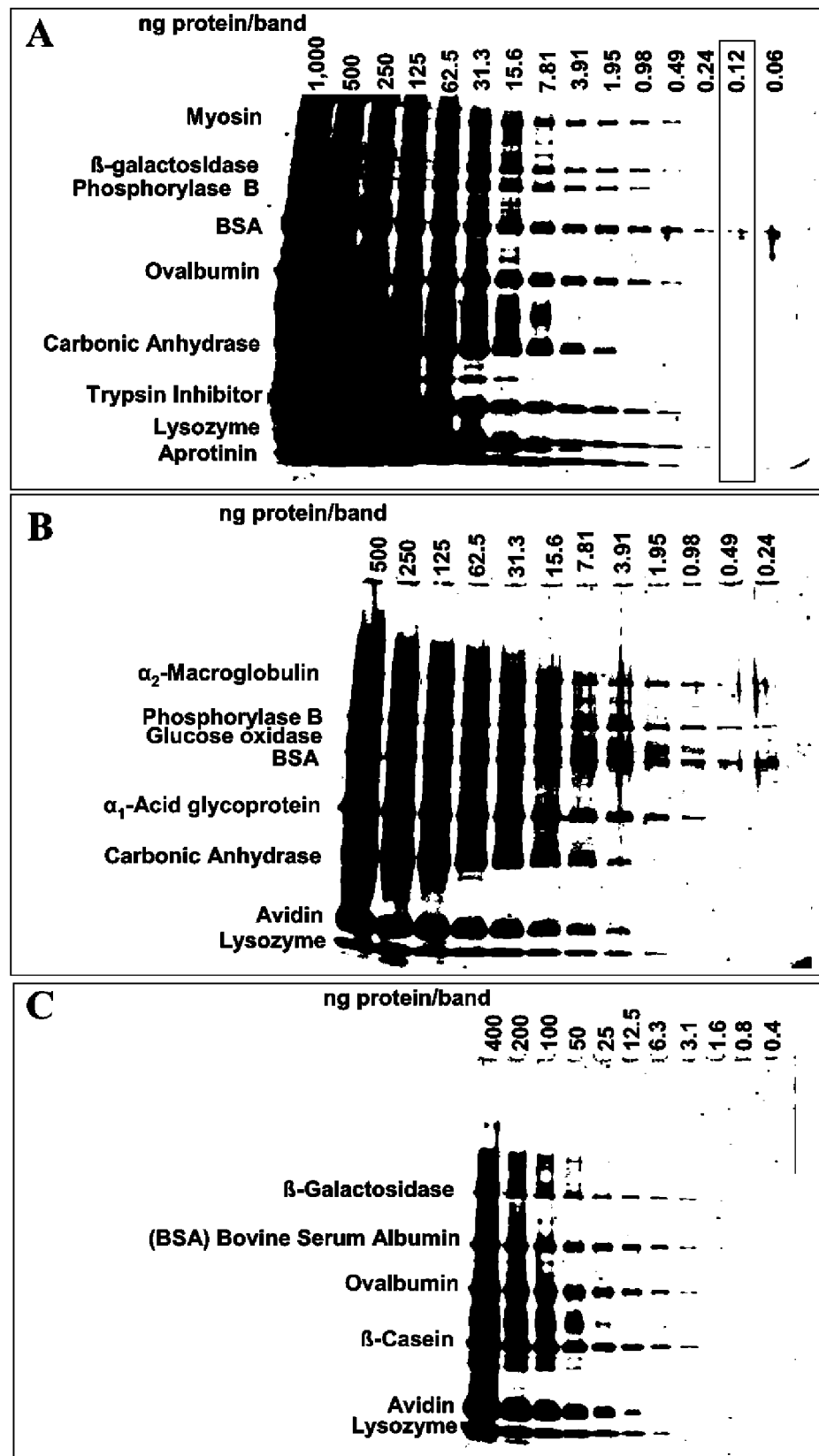
FIG. 9 shows use of one hydroxyquinolone compound as a dye to detect a broad range of commercially available protein standards separated on polyacrylamide gels.

Representative gels were stained with the dyes containing compounds #1, #2, #3, #4, and/or #5 according to methods previously described. FIGS. 9A, 9B, and 9C show results with one exemplary compound (compound #4). The following commercial protein standards were used: Broad Range Protein Standards (Bio-Rad) (FIG. 9A), Glycoprotein Standard Mix (Molecular Probes) (FIG. 9B), and Phosphoprotein Mix (Molecular Probes) (FIG. 9C). The Broad Range Protein Standard was serially diluted and loaded onto 4-20% Tris-glycine SDS-polyacrylamide gels (Invitrogen) in amounts of 1,000 ng/lane; 500 ng/lane; 250 ng/lane; 125 ng/lane; 62.5 ng/lane; 31.3 ng/lane; 15.6 ng/lane; 7.8 ng/lane; 3.9 ng/lane; 1.95 ng/lane; 0.98 ng/lane; 0.49 ng/lane; 0.24 ng/lane, 0.12 ng/lane, and 0.06 ng/lane. The Glycoprotein Standard was serially diluted and loaded onto 4-20% Tris-glycine SDS-polyacrylamide gels (Invitrogen) in amounts of 500 ng/lane; 250 ng/lane; 125 ng/lane; 62.5 ng/lane; 31.3 ng/lane; 15.6 ng/lane; 7.8 ng/lane; 3.9 ng/lane; 1.95 ng/lane; 0.98 ng/lane, 0.49 ng/lane, and 0.24 ng/lane. The Phosphoprotein Standard was serially diluted and loaded onto 4-20% Tris-glycine SDS-polyacrylamide gels (Invitrogen) in amounts of 400 ng/lane; 200 ng/lane; 100 ng/lane; 50 ng/lane; 25 ng/lane; 12.5 ng/lane; 6.25 ng/lane; 3.1 ng/lane; 1.56 ng/lane; 0.78 ng/lane, and 0.39 ng/lane. Proteins on all gels were separated by electrophoresis.

Following electrophoresis, gels containing separated proteins were placed in a clean tray and washed two times for thirty minutes each with 35 mL 40% v/v ethanol, 10% v/v acetic acid. The gels were then washed for five minutes in water. After the water wash, 35 ml of the 1× stain reagent (55 mM sodium acetate, pH 4; 0.3% w/v PEG, 5% v/v 1,2-propanediol, 0.49% v/v ethanol, 50 mM benzaldehyde, and 165 nM compound #4) was added to the tray containing the washed gel and incubated for one hour with gentle mixing. After staining, the gel was washed with 35 ml 5% v/v acetic acid for five minutes, followed by two consecutive fifteen minute water washes. The gel was imaged on a Typhoon 9410 variable mode imager (GE Healthcare) at 532 nm excitation and 580 bandpass (BP) 30 emission filter, and a PMT setting of 600 V.

The stain detected a diverse selection of proteins including phosphoproteins (ovalbumin, β-casein) and glycoproteins ($\alpha_2$-macroglobulin, glucose oxidase, $\alpha_1$-acid glycoprotein, avidin). The detection sensitivity was, at minimum, 1 ng protein per band, but select proteins were detected at a sensitivity of 0.1 ng protein per band. The stain reagent detected most proteins when 0.12 ng protein was loaded onto the gels. Results at this concentration are shown as the boxed lane in FIG. 9A. Proteins in the glycoprotein mix were detected at a sensitivity of 1 ng for all proteins, and at a sensitivity of 0.5 ng or less for higher molecular weight proteins such as α-acid glycoprotein (FIG. 9B). Proteins in the phosphoprotein mix were detected at a sensitivity of 1.6 ng or less (FIG. 9C). Variability in detection sensitivity may be a result of slight differences in the protein concentrations of the standards (e.g., a 1% variance in a 1,000 ng protein solution is 10 ng) or due to steric hindrance issues caused by posttranslational modifications such as glycosylation or phosphorylation. These modifications may reduce binding of the dye to the amino acids in the protein.

Example 2

Commercially available HeLa cells and rat heart tissue were lysed (using M-PER, Pierce) and protein content of the lysates was determined by BCA protein assay (Pierce). Lysates were diluted in sample buffer containing SDS and 10 mM DTT to 125 ng total protein/µl (HeLa cell lysates) and 62.5 ng total protein/µl (rat heart tissue). The lysates were serially diluted and 10 µl of each sample was loaded on a 4-20% Tris-glycine SDS gel, and proteins were separated by electrophoresis. Following electrophoresis, gels containing separated proteins were fixed with two, thirty minute washes in 40% ethanol, 10% acetic acid. The gels were then washed for five minutes with water. Working stain reagent (1×) was prepared by diluting the 10× stain reagent (550 mM sodium acetate, pH 4; 3% w/v PEG, 50% v/v 1,2-propanediol, 4.9% v/v ethanol, 500 mM benzaldehyde, and 1.65 µM compound #4) 1 to 10 in water. The gels were incubated in the 1× working reagent for sixty minutes, washed in 5% acetic acid for five minutes followed by two, fifteen minutes washes in water, and then imaged on a Typhoon 9410 Variable Mode Imager (GE Healthcare) at 532 nm laser, 580 BP 30 emission filter, 600 V PMT.

Figure 10:
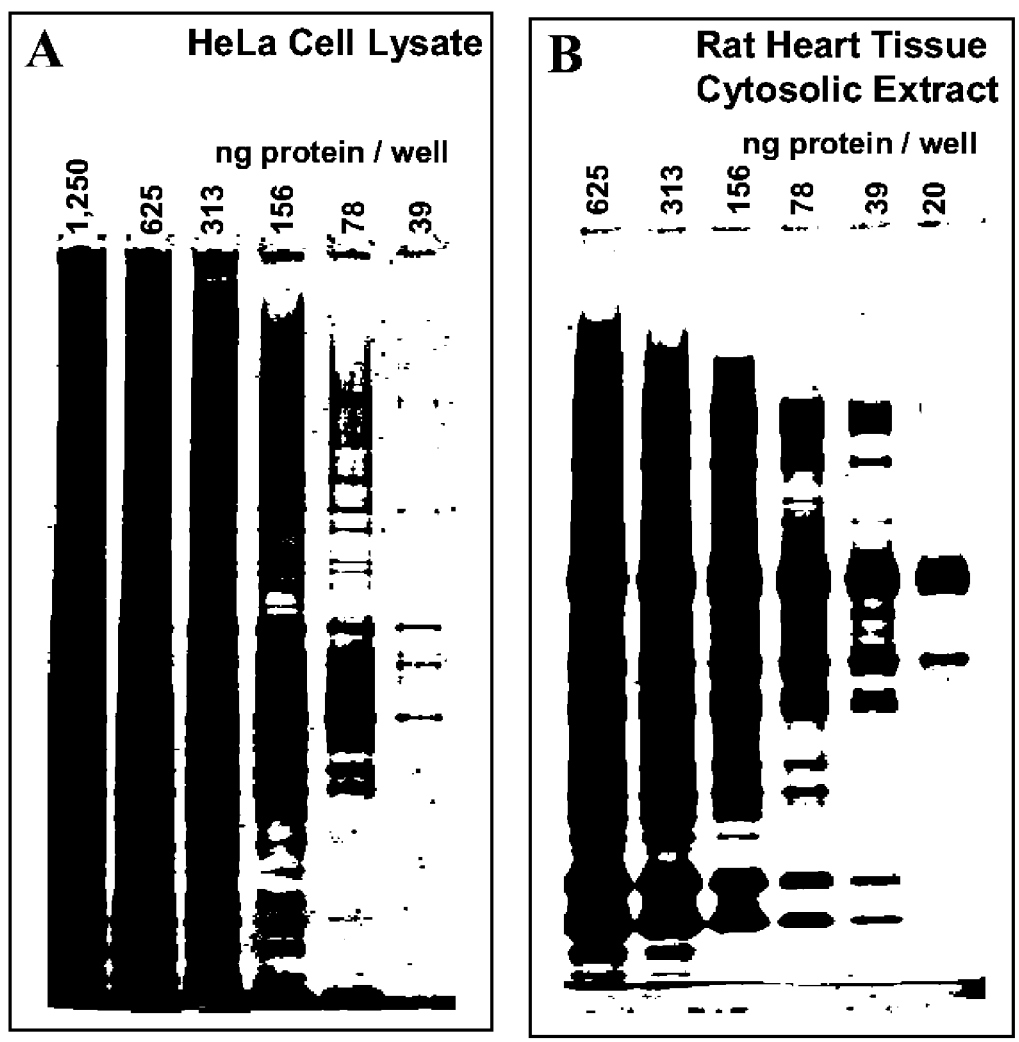
FIG. 10 shows use of one hydroxyquinolone compound as a dye to detect proteins from cell lysates using HeLa cells (FIG. 10A) and rat heart tissue (FIG. 10B).

Results are shown in FIG. 10, with proteins separated from HeLa cell lysates shown in FIG. 10A, and proteins separated from rat heart tissue lysates shown in FIG. 10B. The protein profile of the lysates was observed as a smear, with high abundant proteins appearing as distinct bands. The distinct protein bands were detected at a sensitivity of 39 ng total protein/well or less with the HeLa cell lysate (FIG. 10A), and 20 ng total protein/well or less with the rat heart tissue cytosolic extract (FIG. 10B).

Example 3

HeLa cell lysates were prepared as previously described and equilibrated in 8 M urea, 4% CHAPS using a 2-D Sample Prep for Soluble Proteins (Pierce, #89865). Lysate protein (28 µg), determined by BCA Assay (Pierce #23225), was separated using pH 5-8 IPG strips (Bio-Rad) for isoelectric focusing for the first dimension, and SDS-PAGE on 4-20% Tris-HCl gels (Bio-Rad) for the second dimension. The gels were stained according to the manufacturer's recommended protocols, and stained gels were imaged using a Typhoon 9410 Variable Mode Imager (GE Healthcare) at the excitation/ emission settings providing the best sensitivity for each stain. The positive electrode was on the left and negative on the right.

Figure 11:
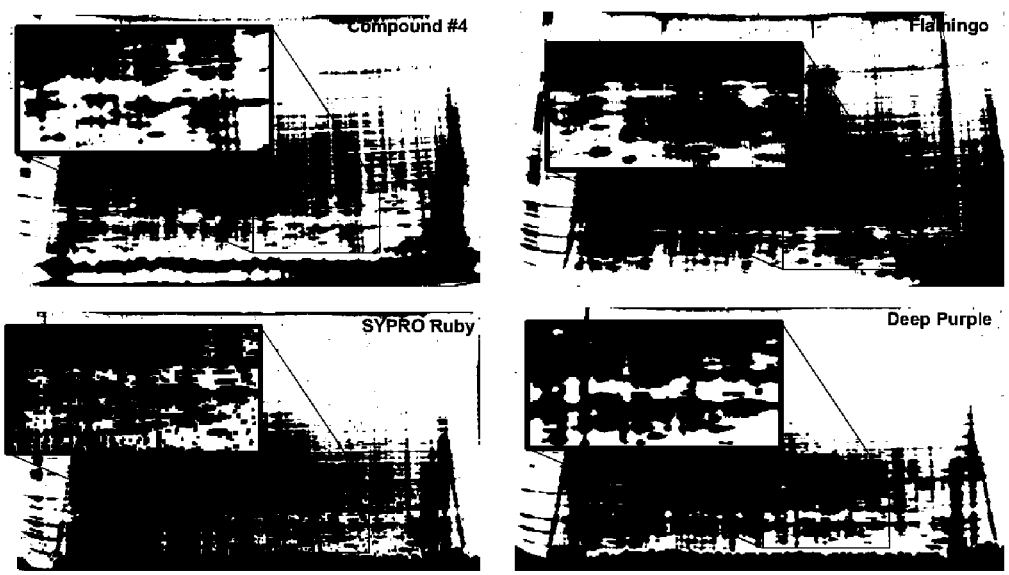
FIG. 11 shows use of one hydroxyquinolone compound as a dye, and commercially available protein dyes, to detect proteins separated on gels by two-dimensional electrophoresis.

Results are shown in FIG. 11, with compound #4 used as the fluorescent protein stain reagent. Compared to commercial stains Flamingo (Bio-Rad), SYPRO-Ruby (Invitrogen), and Deep Purple (GE Healthcare), compound #4 provided equivalent or superior performance for proteins separated by two dimensional electrophoresis. Compound #4 resulted in sharper more intense detection of the proteins, less protein-to-protein variability and a wider dynamic range of detection.

Example 4

To determine the extent of linearity of protein standard curves using a representative compound in the fluorescent protein stain reagent, selected proteins available as commercial protein standards were serially diluted. Each protein set was separated by electrophoresis on either Novex 4-20% Tris-glycine SDS gels (Invitrogen) or Criterion 4-20% Tris-HCl SDS gels (Bio-Rad) creating a concentration gradient of protein bands. Gels containing separated proteins were stained with the fluorescent protein stain reagent containing compound #4 and imaged on a Typhoon 9410 Variable Mode Imager (GE Healthcare) at 532 nm laser, 580 BP 30 emission filter, 600 V PMT.

Figure 12:
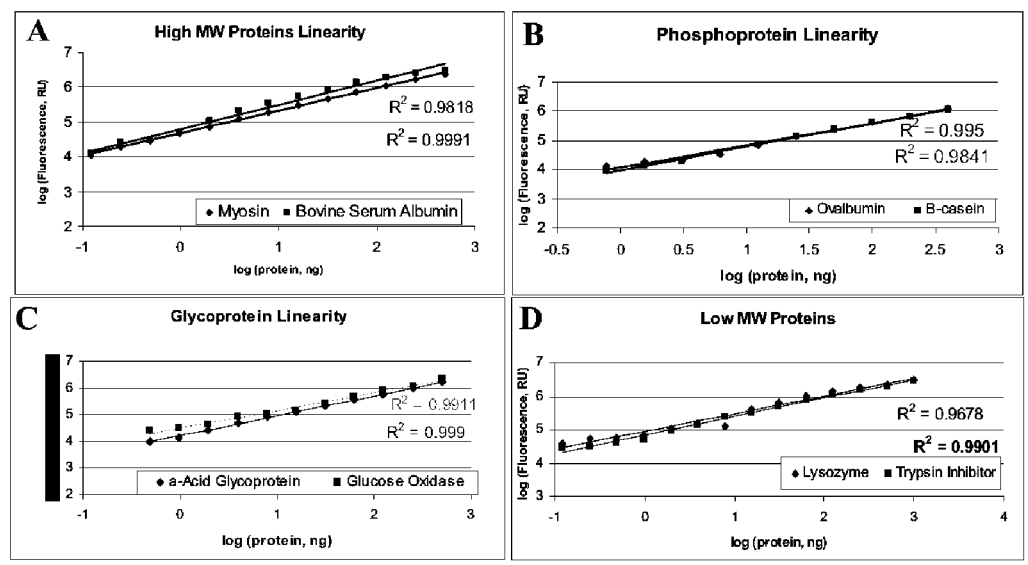
FIG. 12 graphs fluorescent output using one hydroxyquinolone compound as a dye versus protein concentration using high molecular weight proteins (FIG. 12A), phosphoproteins (FIG. 12B), glycoproteins (FIG. 12C), and low molecular weight proteins (FIG. 12D).

The relative fluorescent intensity of the separated protein bands was determined using ImageQuant software. The log of the relative intensity was plotted versus the log of the protein band concentration. The best fit line was determined by linear regression and the $R^2$ value is indicated for each line, as shown in FIG. 12 using myosin and bovine serum albumin as examples of high molecular weight proteins (FIG. 12A), ovalbumin and β-casein as examples of phosphoproteins (FIG. 12B), α-acid glycoprotein and glucose oxidase as examples of glycoproteins (FIG. 12C), and lysozyme and trypsin inhibitor as examples of low molecular weight proteins (FIG. 12D).

The linear quantification range of all proteins stained with the fluorescent protein stain reagent extended over at least three orders of magnitude. Specific proteins such as myosin and bovine serum albumin (FIG. 12A), lysozyme and trypsin inhibitor (FIG. 12D) were quantified over four orders of magnitude.

Example 5

The fluorescent protein stain reagent was reversible and compatible with MALDI-MS analysis.

Bovine serum albumin (200 ng) (FIGS. 13A, 13B) or horse heart myoglobin (200 ng) (FIGS. 13C and 13D) was loaded on 4-20% Tris glycine gels and separated by electrophoresis. Gels containing the separated proteins were stained using a representative compound as the fluorescent protein stain reagent (75 mM sodium propionate, pH 4, 4.9% ethanol, 5% 1,2-propanediol, 0.3% w/v polyethylene glycol, 50 mM benzaldehyde, 75 ng/ml compound #4). The commercially available stain SYPRO Ruby (Invitrogen) was used for comparison.

Bands containing separated proteins were excised from gels as gel plugs, protein was digested with trypsin, and the peptide fragment digests were extracted using methods known to one skilled in the art. The resulting peptide fragments were further purified with Zip Tips (Milli Pore) and spotted for MALDI-MS analysis in matrix (2 mg/ml α-cyano-4-hydroxycinnamic acid, 50% acetonitrile, and 0.1% trifluoroacetic acid).

Figure 13:
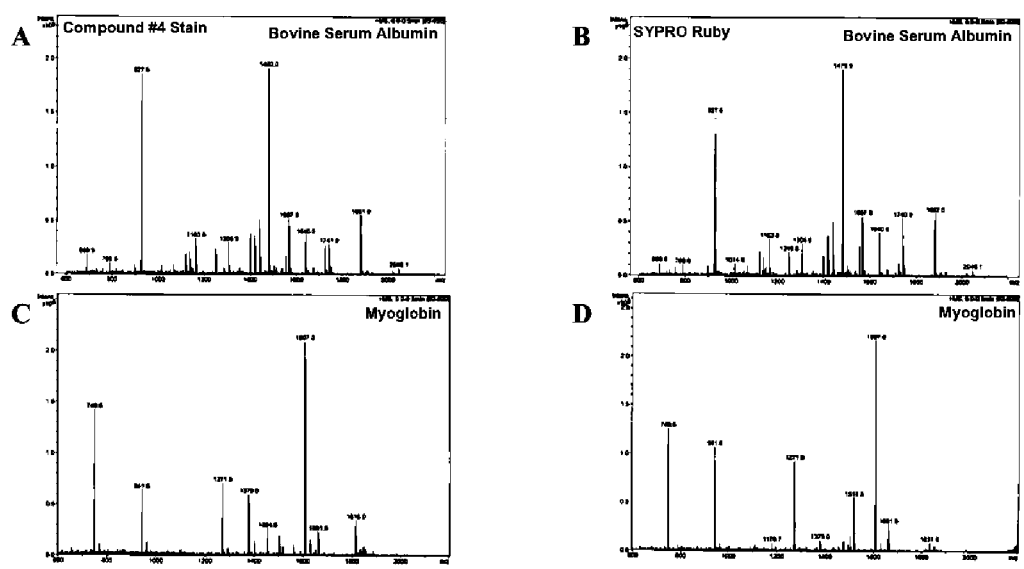
FIG. 13 shows matrix-assisted laser desorption/ionization-mass spectra (MALDI-MS) of proteins stained by hydroxyquinolone dyes (FIGS. 13A, 13C) and a commercial stain (FIGS. 13B, 13D).

Results are shown in FIG. 13. Characteristic peaks were observed for digests from bovine serum albumin (FIG. 13A) and myoglobin (FIG. 13B) stained with the fluorescent protein stain reagent. Digests from bovine serum albumin (FIG. 13C) and myoglobin (FIG. 13D) stained with commercially available SYPRO Ruby. Identical mass peak profiles were observed for proteins stained with the fluorescent protein stain (compound #4) and SYPRO Ruby. The mass peaks corresponded to the tryptic peptide fragments and did not exhibit any mass increase that would be representative of the dye mass.

Example 6

The hydroxyquinolone fluorescent protein stain reagents provided equivalent or superior protein staining and detection in less time compared to existing fluorescent stains.

Figure 14:
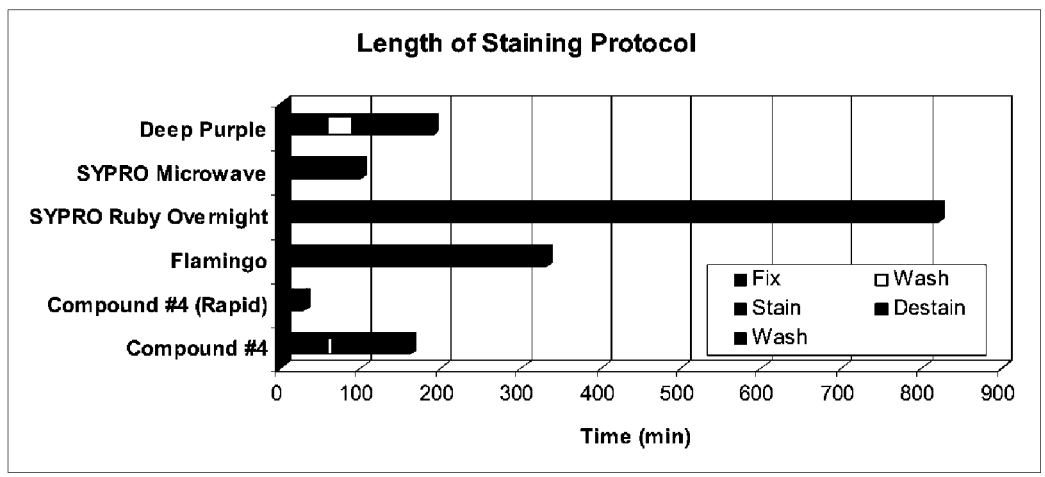
FIG. 14 shows incubation times to stain proteins using one hydroxyquinolone compound as a dye and other commercially available fluorescent protein stains.

FIG. 14 shows the time required to stain proteins using a number of commercially available protein stains compared to a representative compound (compound #4) formulated as a fluorescent protein stain reagent. In one embodiment, staining with the hydroxyquinolone stain reagent required 160 minutes.

In one embodiment, all gels containing separated proteins were fixed in 40% v/v ethanol, 10% v/v acetic acid for two, thirty minutes washes, followed by a five minute water wash. Gels were then stained for one hour in the 1× working stain reagent. Stained gels were washed in 5% acetic acid for five minutes and two, fifteen minute water washes to remove background staining. In another embodiment, all gels containing separated proteins were fixed in 40% v/v ethanol, 10% v/v acetic acid for two, five minute washes, followed by a one minute water wash. Gels were then stained for fifteen minutes in the 1× working stain reagent. Stained gels were washed for three minutes in water to remove background staining. This embodiment required a total stain time of about thirty minutes. Protein detection was at a sensitivity of about 10 ng protein. As shown in FIG. 14, the gel processing and handling time required for protein detection with compound #4 was less than that required with other fluorescent stains.

Example 7

Figure 15:
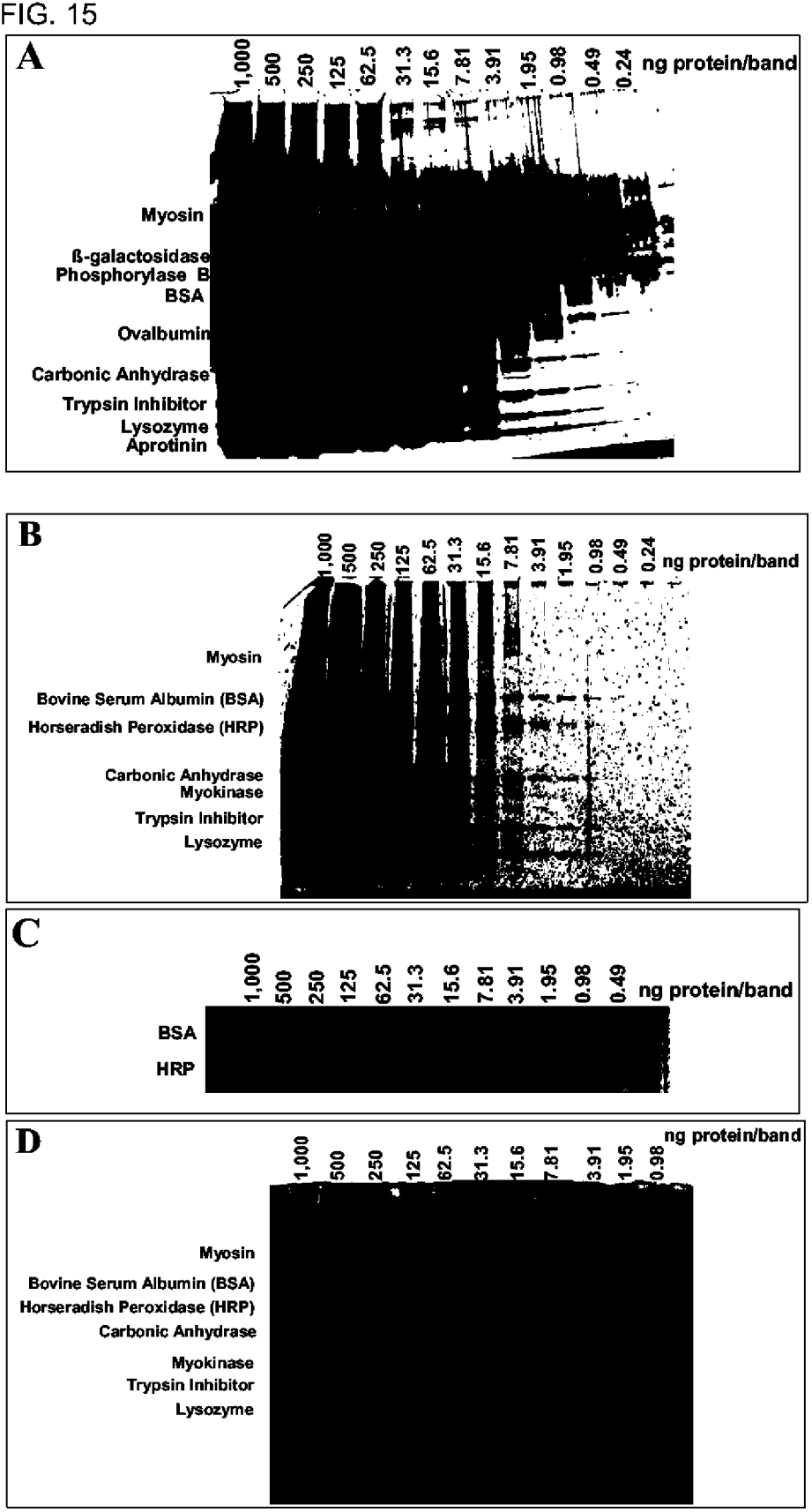
FIG. 15 shows use of hydroxyquinolone dyes to detect a broad range of proteins with multiple polyacrylamide gel formats (FIGS. 15A, 15B, 15C, 15D).

The fluorescent protein stain reagent detected a broad range of proteins using multiple polyacrylamide gel formats. Serial dilutions of commercially available protein standards, previously described, were separated by electrophoresis on the following gels, with the results shown in FIG. 15: Criterion 4-20% Tris-HCl (Bio-Rad) (FIG. 15A); Precise 4-20% Tris-HEPES (Pierce) (FIG. 15B); laboratory prepared 12% bis-acrylamide (bis-acrylamide, Tris buffers, TEMED, and ammonium persulfate from Bio-Rad) (FIG. 15C); and 12% NuPage gel, MES buffer (Invitrogen) (FIG. 15D). Gels containing separated proteins were stained with the fluorescent protein stain reagent containing compound #4 and imaged on a Typhoon 9410 Variable Mode Imager (GE Healthcare) using 532 nm laser, 580 BP 30 emission filter and a PMT setting of 600 V. The results demonstrate compatibility of the compound #4 stain with various gel types and formats.

Example 8

The fluorescent protein stain reagent was selective for proteins over nucleic acids. Two 6% polyacrylamide DNA retardation gels were loaded with a 100 bp DNA ladder and a broad range protein standard. Electrophoresis was performed in 0.5×TBE running buffer at pH 8.3.

Figure 16:
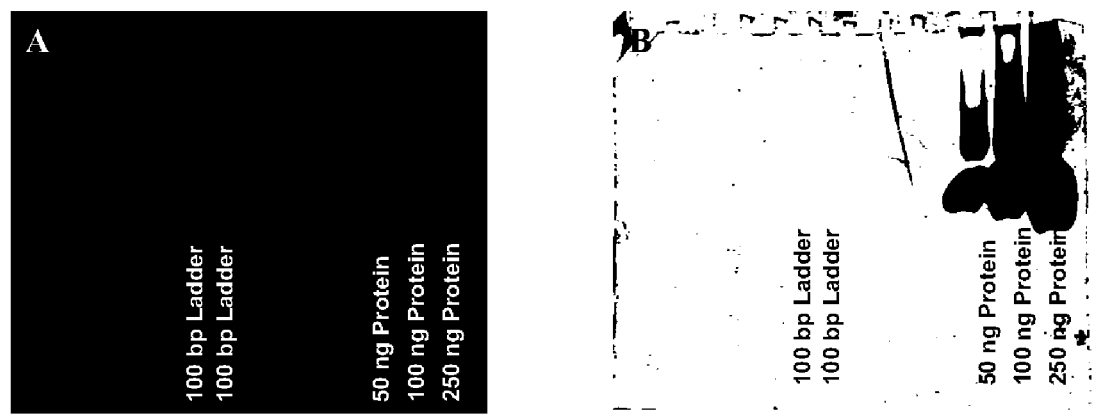
FIG. 16 shows gels on which protein and nucleic acid were separated and stained by ethidium bromide (FIG. 16A) and hydroxyquinolone dyes (FIG. 16B).

One gel containing separated proteins and nucleic acids was stained with ethidium bromide and visualized on a UV lightbox, with results shown in FIG. 16A. This gel served as the positive control, indicating the presence of DNA in the gel.

The other gel containing separated proteins and nucleic acids was stained with the 1× hydroxyquinolone stain reagent containing compound #4 and imaged on a Typhoon 9410 Variable Mode Imager (GE Healthcare) using 532 nm laser, 580 BP 30 emission filter and a PMT setting of 600 V, with results shown in FIG. 16B.

The fluorescent protein stain reagent detected the protein standard but did not detect the DNA ladder. The results indicated that the hydroxyquinolone stain was specific for amino acids and proteins.

Example 9

Figure 17:
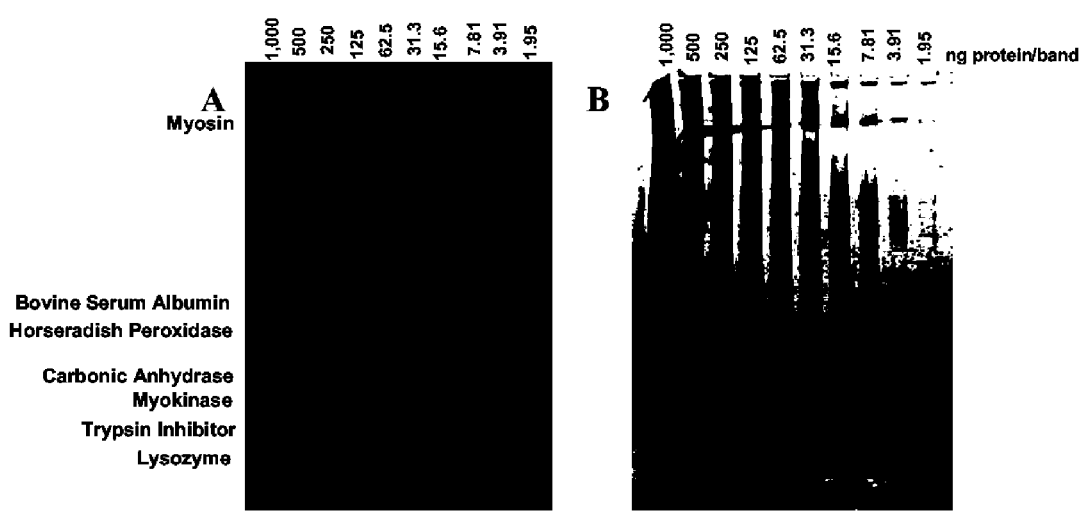
FIG. 17 shows gels on which proteins had been separated, stained by hydroxyquinolone dyes, and imaged by two imaging modalities (FIGS. 17A, 17B).

The fluorescent protein stain reagent was compatible with multiple imaging platforms, including but not limited to a CCD imager, a laser based scanner, and a UV transilluminator, with results shown in FIG. 17.

Protein standards were separated by electrophoresis in a 4-20% Tris-glycine gel and stained with the fluorescent protein stain reagent (75 mM sodium propionate, pH 4, 4.9% ethanol, 5% 1,2-propanediol, 0.3% w/v polyethylene glycol, 50 mM benzaldehyde, 75 ng/ml compound #4). The gel containing separated proteins was imaged on a Kodak 200 mm Imager using a 535 nm excitation filter, 600 nm emission filter with a five minute exposure (FIG. 17A), and a Typhoon 9410 Variable Mode Imager (GE Healthcare) using 532 nm laser, 580 BP 30 emission filter and a PMT setting of 600 V (FIG. 17B). Protein bands were detected at a sensitivity of 1.95 ng or less when stained with the compound #4 fluorescent protein stain and imaged with either a CCD or laser based imaging platform.

Example 10

Figure 18:
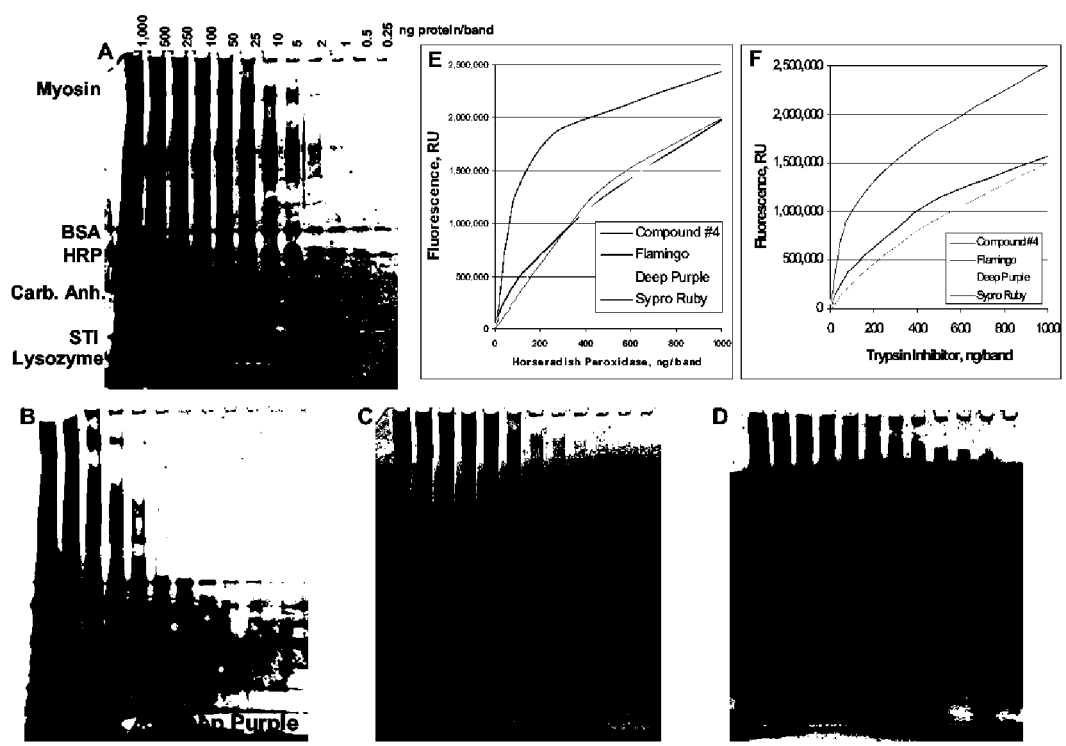
FIG. 18 shows gels on which proteins had been separated and stained by one hydroxyquinolone dye and commercial dyes.

A protein standard was prepared using myosin, bovine serum albumin, horseradish peroxidase, carbonic anhydrase, soybean trypsin inhibitor, and lysozyme. This protein standard was serially diluted and loaded onto four Novex 4-20% Tris-glycine gels (Invitrogen) in amounts of 1,000 ng/lane; 500 ng/lane; 250 ng/lane; 100 ng/lane; 50 ng/lane; 25 ng/lane; 10 ng/lane; 5 ng/lane; 2 ng/lane; 1 ng/lane; 0.5 ng/lane, and 0.25 ng/lane. Proteins were separated by electrophoresis. Gels containing separated proteins were stained with a representative compound (compound #4) formulated as a fluorescent protein stain reagent (FIG. 18A) or one of the following commercially available stains: Deep Purple (GE Healthcare) (FIG. 18B), SYPRO Ruby (Invitrogen) (FIG. 18C), or Flamingo (Bio-Rad) (FIG. 18D), according to the manufacturer's recommended protocol.

Gels were imaged using a Typhoon 9410 Variable Mode Imager (GE Healthcare) at the excitation/emission settings providing the best sensitivity for each stain. The fluorescent intensities for bands containing horseradish peroxidase and soybean trypsin inhibitor were determined using ImageQuant Analysis software. The fluorescent intensity was plotted against the protein concentration for each stain, with results shown in FIG. 18E for horseradish peroxidase, and FIG. 18F for trypsin inhibitor.

The fluorescent protein stain reagent was comparable to the commercially available stains with respect to level of detection. The fluorescent protein stain reagent detected proteins at a sub-nanogram sensitivities, while not saturating the fluorescent signal of more concentrated protein bands.

Example 11

Serial dilutions of a SDS-PAGE protein standard for SYPRO Orange Stain Broad Range (Bio-Rad) were loaded on Criterion 4-20% Tris-HCl gels (Bio-Rad) in amounts ranging from 1,000 ng/lane to 0.12 ng/lane. Proteins were separated by electrophoresis and stained according to manufacturer's recommended protocol or using the fluorescent protein stain reagent containing compound #4, as described above. Gels were imaged using a Typhoon 9410 Variable Mode Imager (GE Healthcare) at the excitation/emission settings providing the best sensitivity for each stain.

Figure 19:
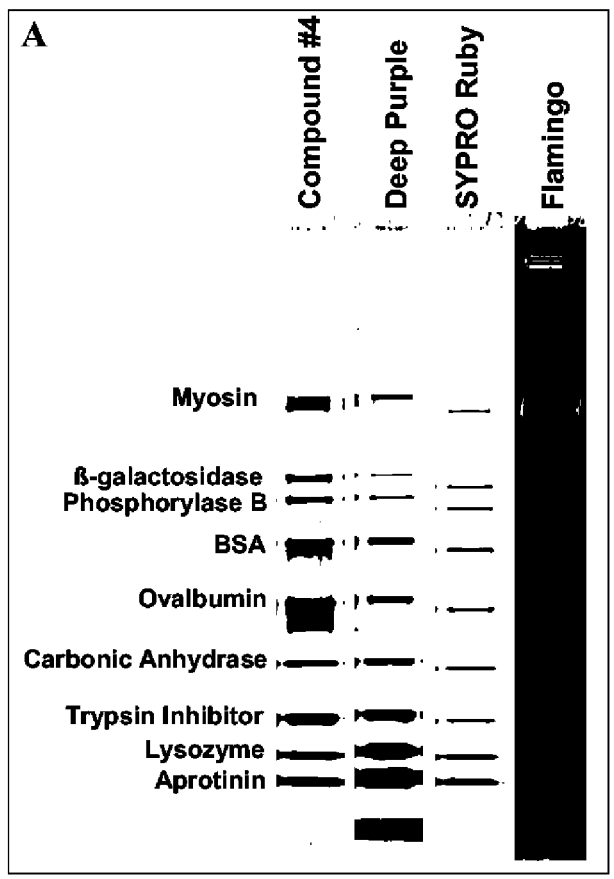
FIG. 19 shows a gel (FIG. 19A) and a graph (FIG. 19B) of relative fluorescence intensities for proteins stained with one hydroxyquinolone dye and commercial dyes.
Figure 19:
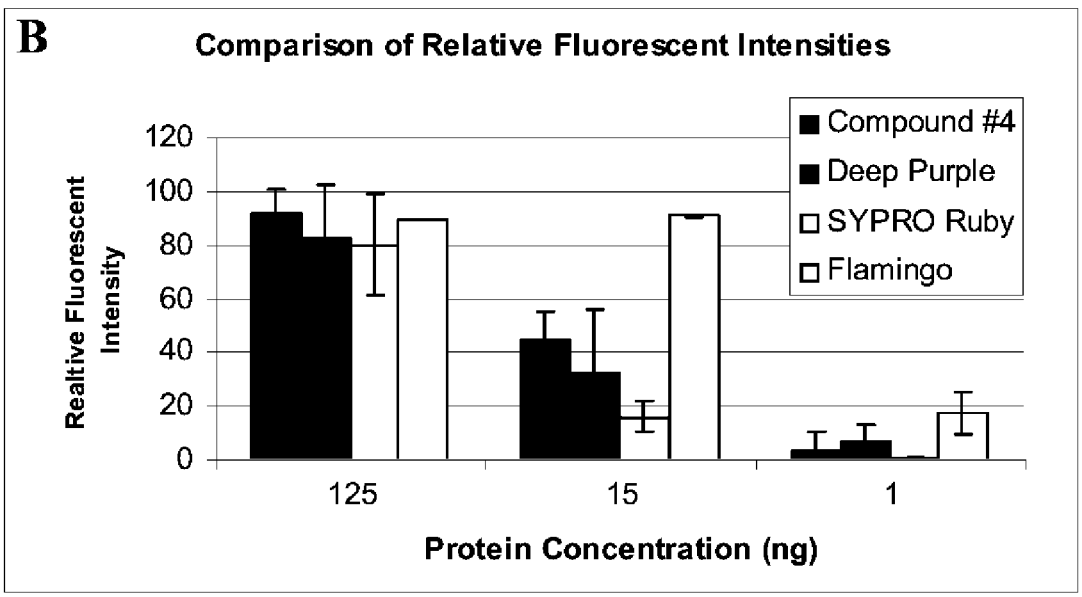

FIG. 19A shows the lane that had been loaded with 15.6 ng protein and stained using compound #4 formulated as a fluorescent protein stain reagent, Deep Purple (GE Healthcare), SYPRO Ruby (Invitrogen), or Flamingo (Bio-Rad). Fluorescent intensity was determined using the ImageQuant Analysis software. FIG. 19B shows a graph of the intensity of each stained protein band in each of the 125 ng lane, the 15 ng lane, and the 1 ng lane; results were averaged and the standard deviations calculated and plotted.

Flamingo stain had the highest signal but a lower linear range. Deep Purple stain had the largest standard deviation or variability among proteins. The fluorescent protein stain reagent (compound #4) had both a high signal intensity and a broad quantitative range.

Example 12

Figure 24:
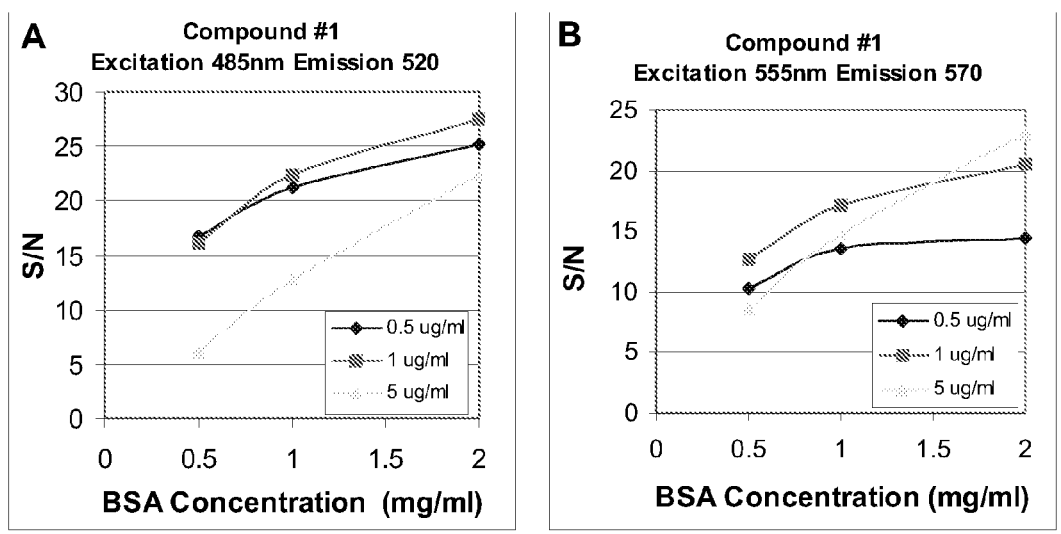
FIG. 24 shows the use of one hydroxyquinolone compound for detecting proteins in solution in a multiwell format.

Compound #1 was dissolved in dimethylformamide (DMF) at 1 mg/ml and diluted to 10 μg/ml, 5 μg/ml, and 2.5 μg/ml in 50 mM sodium acetate buffer, pH 4.0. One hundred and fifty μl of each dilution was added to four separate wells of a 96-well black microtiter plate. To one well containing each of these dilutions of the assay reagent, 25 μl of bovine serum albumin (prepared in 150 mM NaCl/0.02% sodium azide solution) was added at 2 mg/ml, 1 mg/ml, and 0.5 mg/ml respectively. The plate was read immediately using the Tecan Saffire instrument at 485 nm excitation and 520 nm emission with a gain of 116 (FIG. 24A) and at 555 nm excitation and 570 nm emission with a gain of 112 (FIG. 24B). Compound #1 exhibited increasing signal to noise (S/N) ratio with increasing protein concentration. The 5 μg/ml dye (compound #1) had the best differential response to increasing protein concentration.

The above examples and descriptions demonstrate that the fluorescent protein dye was able to stain a diverse set of proteins such as phosphoproteins, glycoproteins, and proteins derived from cell lysates. It was compatible with proteins separated by electrophoresis on both 1-dimensional and 2-dimensional gels and proteins in solution. It permitted protein quantitation over four orders of magnitude, and linear quantitation over at least three and, for some proteins, of at least four orders of magnitude. The fluorescent protein stain reagent exhibited sensitivity equal to or greater than commercially available stains, based on a broad range of proteins in 1-dimensional gels, and typically allowed detection to less than 0.25 ng protein. The fluorescent protein stain reagent selectively stained proteins over nucleic acids, and was compatible with MALDI-MS analysis and multiple gel types and imaging platforms.

Other variations or embodiments of the invention will also be apparent to one of ordinary skill in the art from the above figures, description, and examples. Thus, the forgoing embodiments are not to be construed as limiting the scope of this invention.

What is claimed is:

1. A method of staining at least one protein, the method comprising
providing a composition comprising at least one of compounds #2, #3, #4, #5 and modifications thereof in an effective concentration and benzaldehyde, to a protein under conditions sufficient for binding the compound to the protein, and
detecting the protein-bound compound, where compound #2 is

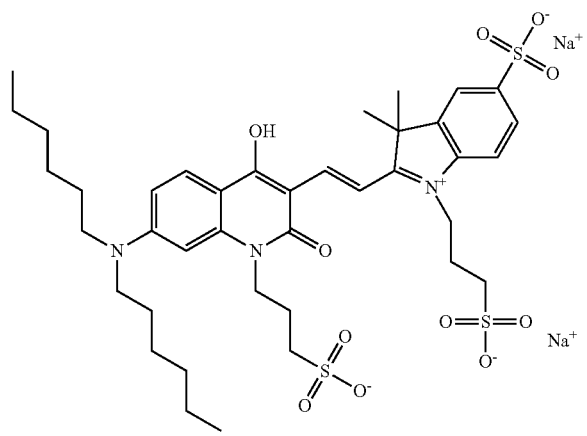

compound #3 is

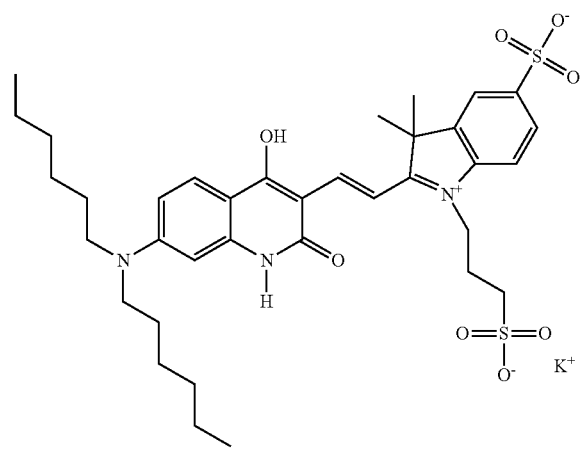

compound #4 is

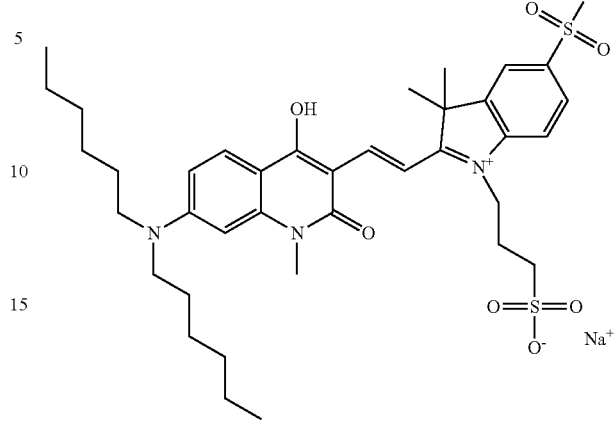

and
compound #5 is

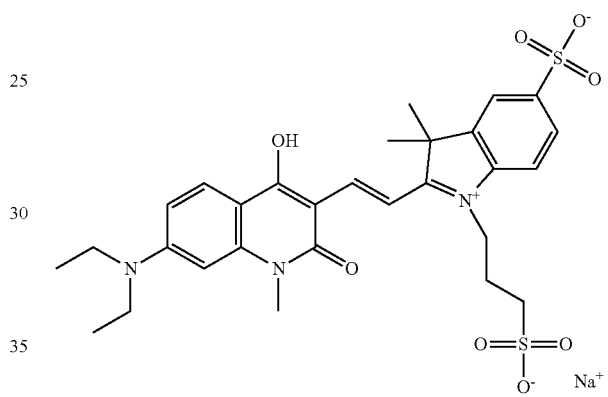

wherein the modification adds a hydrophobic group selected from the group consisting of
(a) at least one of a hydrophobic non-sulfonated compound, hydrophobic alkyl chains, a hydrophobic monosulfonated compound, a di-sulfonated compound, or a tri-sulfonated compound;
(b) an N substituted hydroxyquinolone ring, the N substitution selected from at least one of alkylsulfonate, H, or a $C_1$-$C_{10}$ hydrocarbon;
(c) an alkylsulfonate substituted for at least one of N in the indole ring or sulfonate substituted C in the benzene ring;
(d) at least one $C_4$-$C_{10}$ hydrocarbons on N attached in a 7-position to the benzene ring of the hydroxyquinolone;
(e) 7-N,N-di-hexylamine attached to the hydroxyl-hydroxyquinolone ring or hydrophobic alkyl chains; and combinations thereof, and
where detecting the protein-bound compound results in a qualitative and/or quantitative enhanced determination of the at least one protein over determination in the absence of the excipient.

2. The method of claim 1 wherein the protein includes a polypeptide.

3. The method of claim 1 wherein the protein stained is on a solid support, in a gel, or in solution.

4. The method of claim 1 wherein the protein is detected by fluorescence.

5. The method of claim 1 wherein the composition is provided to the protein for about 5 minutes to about 18 hours.

6. The method of claim 1 wherein the compound concentration ranges from about 25 nmol/L to about 200 nmol/L.

7. The method of claim 1 wherein the compound concentration is either about 1.65 μM resulting in a 10× solution and diluting the 10× solution to a 1× solution before providing to the protein, or the compound concentration is about 165 nM resulting in a 1× solution that is provided to the protein.

8. The method of claim 1 further comprising adding at least one of a buffer, a compound solubilizer, a compound stabilizer, polyethylene glycol, or a diol to the composition.

* * * * *